United States Patent

Chen

[11] Patent Number: 6,117,107
[45] Date of Patent: Sep. 12, 2000

[54] SAFETY SYRINGE FOR INTRAVENOUS INJECTION WITH A GUIDED PLUNGER

[76] Inventor: Long-Hsiung Chen, 5F, No. 91-3, Chung Chen Road, Sec. 1, Taipei, Taiwan

[21] Appl. No.: 09/028,576

[22] Filed: Feb. 24, 1998

[30] Foreign Application Priority Data

Sep. 16, 1997 [CN] China ................... 971169047

[51] Int. Cl.⁷ ................................................. A61M 5/00
[52] U.S. Cl. ............................................ 604/110; 604/195
[58] Field of Search ...................... 604/110, 181, 604/187, 195, 198, 218, 228; 128/919

[56] References Cited

U.S. PATENT DOCUMENTS

| | | | |
|---|---|---|---|
| 5,125,908 | 6/1992 | Cohen | 604/196 |
| 5,171,300 | 12/1992 | Blake, III et al. | 604/110 |
| 5,211,628 | 5/1993 | Marshall | 604/110 |
| 5,242,402 | 9/1993 | Chen | 604/110 |
| 5,328,475 | 7/1994 | Chen | 604/110 |
| 5,401,246 | 3/1995 | Mazur et al. | 604/110 |
| 5,405,327 | 4/1995 | Chen | 604/110 |
| 5,496,278 | 3/1996 | Buff | 604/110 |
| 5,562,627 | 10/1996 | Chen | 604/110 |
| 5,569,203 | 10/1996 | Chen | 604/110 |
| 5,575,774 | 11/1996 | Chen | 604/110 |
| 5,578,015 | 11/1996 | Robb | 604/195 |

*Primary Examiner*—Wynn Wood Coggins
*Assistant Examiner*—Deborah Blyveis
*Attorney, Agent, or Firm*—Rosenberg, Klein & Lee

[57] ABSTRACT

A safety syringe for intravenous injection with a guided plunger is provided that comprises a barrel, a needle unit, and a plunger. An outlet is eccentrically disposed on the top of the barrel. The needle unit includes a needle and a spindle shaped needle holder mounted inside the outlet. A connecting stem has an arrowhead shaped mortise disposed under the spindle shaped needle holder. A plunger has a plunger head on the top thereof with an arrowhead shaped tenon eccentrically disposed thereon. A supporting plate disposed under the plunger head has two guide notches matched with two longitudinal guide strips inside the barrel, so that the arrowhead shaped tenon aligns with the needle unit. After completion of the injection, the arrowhead shaped tenon and the needle unit are connected together, the needle unit can then be pulled into the barrel and subsequently deformed.

1 Claim, 6 Drawing Sheets

A-A

B-B

SAFETY SYRINGE FOR INTRAVENOUS INJECTION WITH A GUIDED PLUNGER

FIELD OF THE INVENTION

The present invention relates to a safety syringe for intravenous injection with a guided plunger. More particularly, the present invention is directed to a syringe where the needle and the needle holder can be pulled into the barrel after use, to prevent an accidental needle stick.

BACKGROUND OF THE INVENTION

In the past, needle stick injuries suffered by medical personnel and others in the course of using intravenous syringes have presented a serious problem. Serious problems such as hepatitis and AIDS may be transmitted by such needle stick injuries, resulting in needless suffering, and possibly even in death. Health care workers are susceptible to accidental needle stick injuries while caring for AIDS or hepatitis patients. Avoiding accidental needle sticks is very important for health care workers.

The needle of a safety syringe is normally provided in a central portion of the syringe, which is suitable for hypodermic or intramuscular injection. However, such a syringe is not suitable for intravenous injection of larger quantities of liquid medicine, filled in a large size syringe. The needle should be eccentrically located with respect to the center line of the syringe, for an ergonomic injection. Therefore, an eccentrically-positioned needle is ergonomically better than a centrally positioned needle of a syringe.

SUMMARY OF THE INVENTION

It is an object of the present invention to provide a safety syringe for intravenous injection with a guided plunger, wherein the bottom of a connecting stem, under the needle holder is formed with an inclined surface so that the needle will be inclined after pulling it into the barrel. Two guide strips are formed inside the barrel toward two notches on a supporting plate, so that the plunger cannot be rotated relative to the barrel and needle.

BRIEF DESCRIPTION OF THE DRAWINGS

The present invention can be better understood by detailed descriptions of the following drawings, in which.

DETAILED DESCRIPTION OF THE INVENTION

Figure 1:
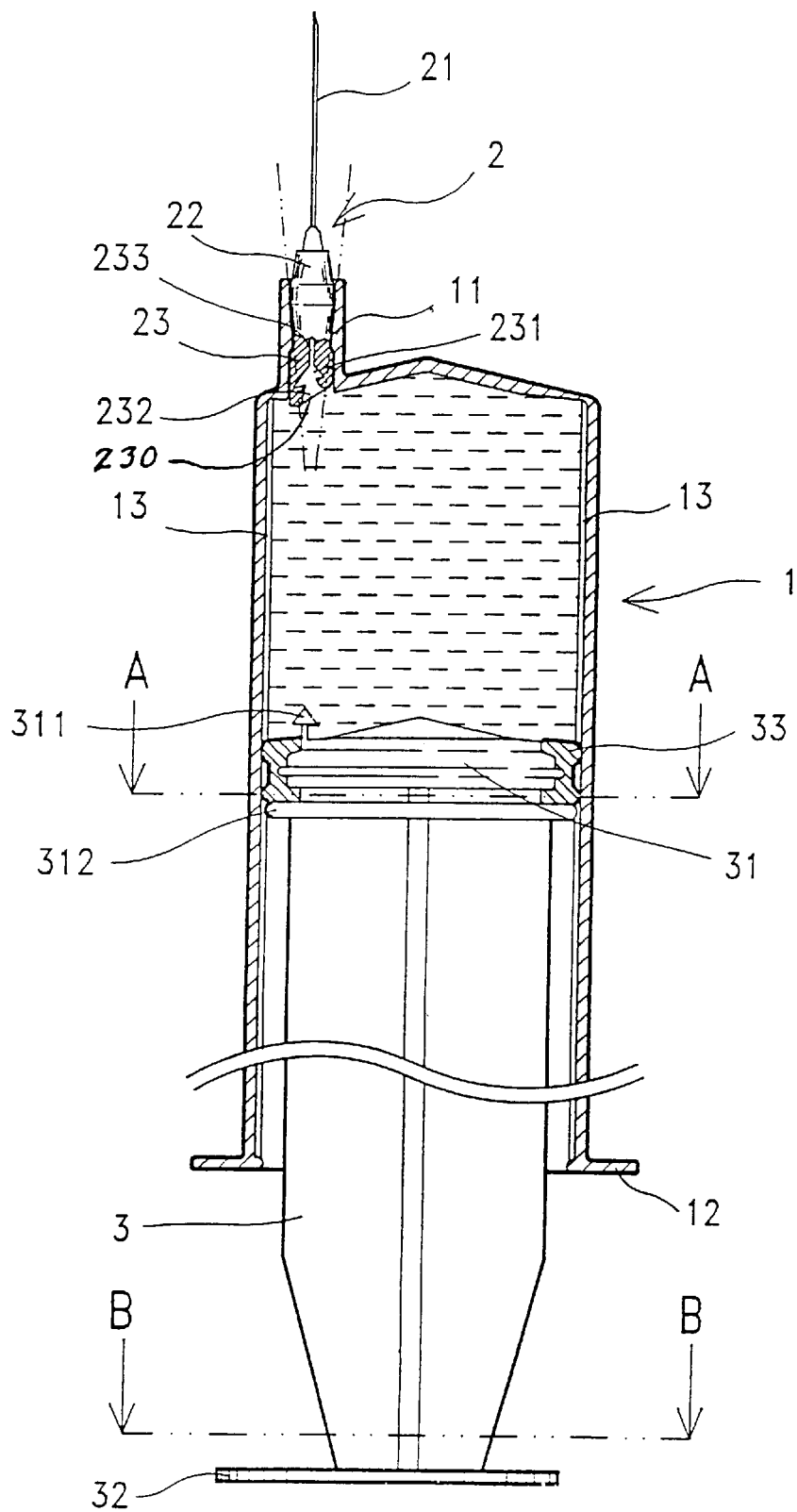
FIG. 1 is a partially sectioned illustration showing the present invention.
Figure 2A:
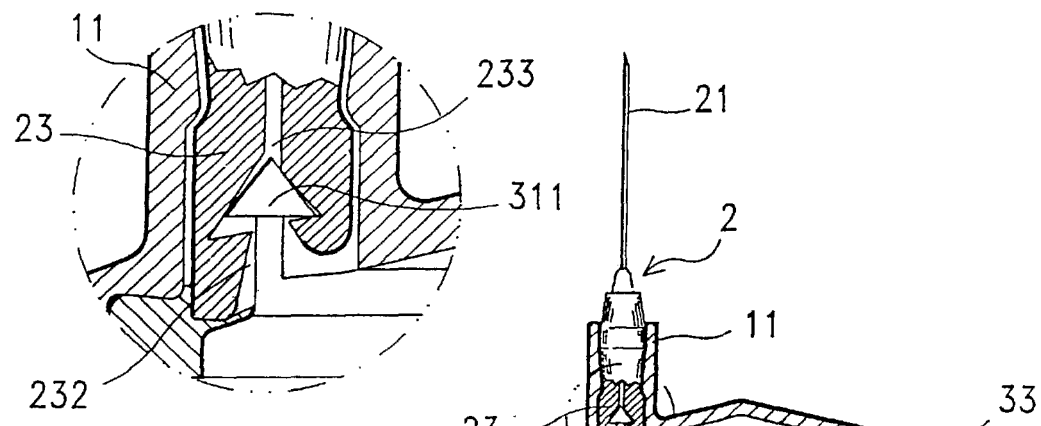
FIG. 2A is an enlarged sectional view of the bottom of the needle holder of FIG. 2.
Figure 3:
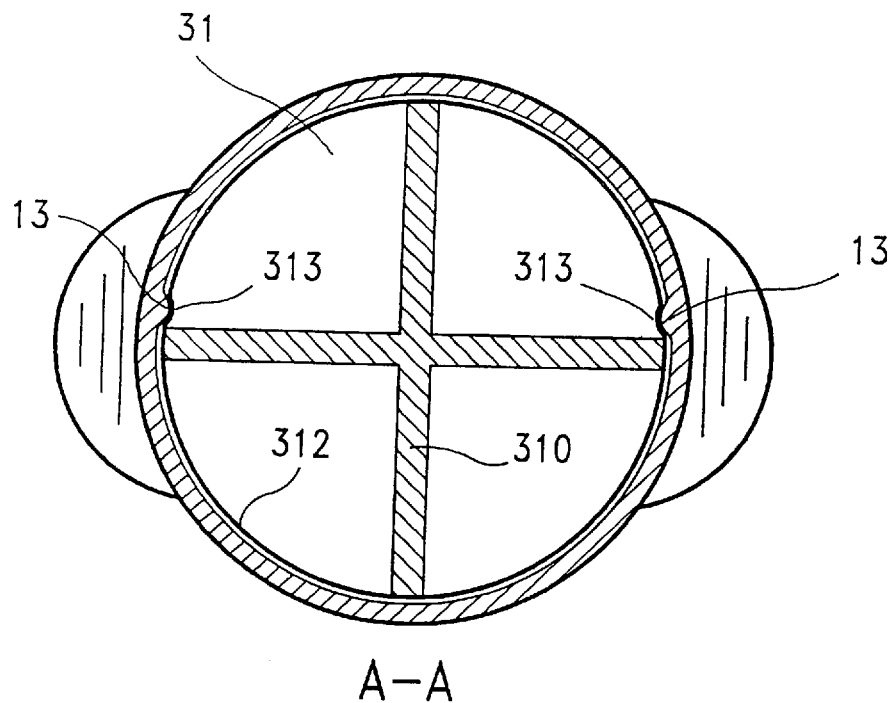
FIG. 3 is a sectional view of the present invention taken along the section line A—A of FIG. 1.
Figure 4:
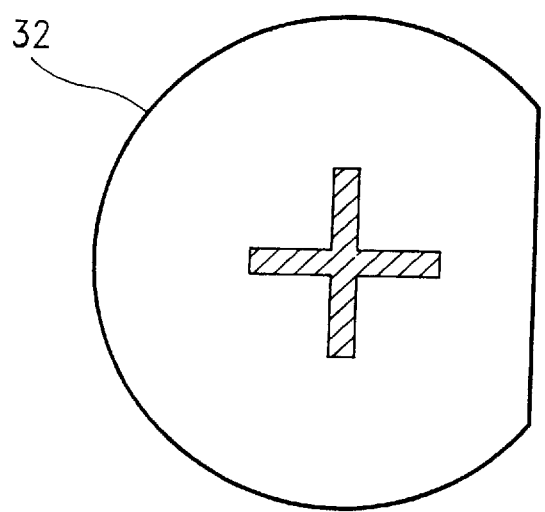
FIG. 4 is a sectional view of the present invention taken along the section line B—B of FIG. 1.

Referring to FIGS. 1, 3 and 4, there is shown the present invention. As shown in FIG. 1, the present invention includes a barrel 1, a needle unit 2, and the plunger 3. The needle unit 2 has a cannulated needle 21, a spindle-shaped needle holder 22 holding the rear portion of the needle 21 therein. A connecting stem 23 extends downwardly from the needle holder 22, the connecting stem having an inclined bottom surface 230 thereat. An inclined arrowhead shaped mortise 231 is disposed in the connecting stem 23 and has a downward flared opening 232 at the inclined bottom surface 230. An upwardly directed through hole 233 (FIG. 2A) extends from a tip end of the arrowhead shaped mortise 231 for leading a medicinal liquid into the cannula of the needle 21. The barrel 1 has a reduced tubular outlet 11 disposed on a conical front portion thereof, for mounting the needle holder 22 therein. An outward flange 12 is disposed at a bottom edge of the rear end of the barrel, and two longitudinal guide strips 13 unsymmetrically disposed on opposite sides of the inner surface of barrel 1. The plunger 3 comprises a plunger head 31 having an arrowhead shaped tenon 311 eccentrically disposed on a conical top surface thereof. A supporting plate 312 is disposed under the plunger head 31 and has two guide notches 313 engaged with the guide strips 13. The plunger rod 310 has a cross-sectional contour and extends from the plunger head 31 to an end plate 32. A sealing ring 33 is inlaid into the periphery of the plunger head 31 and is supported by the supporting plate 312.

Figure 2:
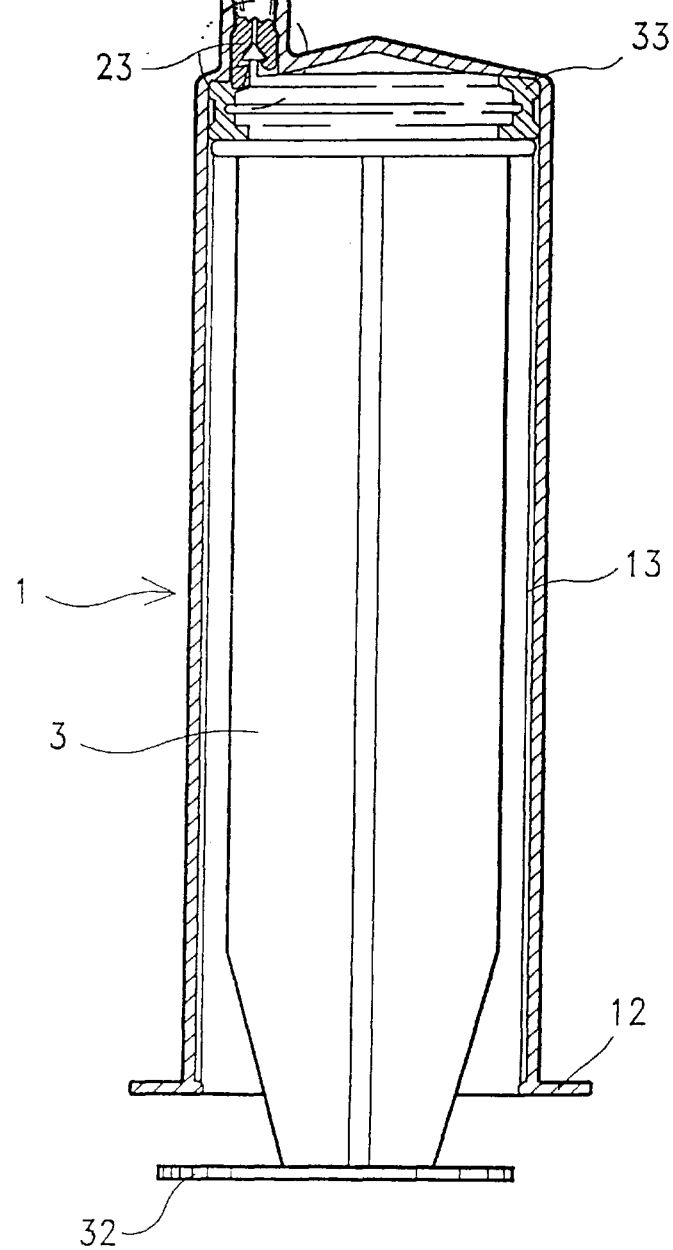
FIG. 2 is an illustration showing the present invention at the completion of an injection.

Referring additionally to FIG. 2, there is shown the present invention when the injection has finished. The plunger 3 is pushed forward so that the arrowhead shaped tenon 311 is connected with the arrowhead shaped mortise 231 of the connecting stem 23.

As shown in FIG. 3, two guide notches 313 formed in the supporting plate 312 of the plunger 3 are engaged with the guide strips 13 inside of the barrel. When the plunger 3 is pushed forwardly by a user's finger, the plunger 3 cannot be rotated so as to keep the alignment between the arrowhead shaped tenon 311 and the mortise 231 for coupling therebetween through the flange opening 232 of the connecting stem 23.

Figures 5, 5A:
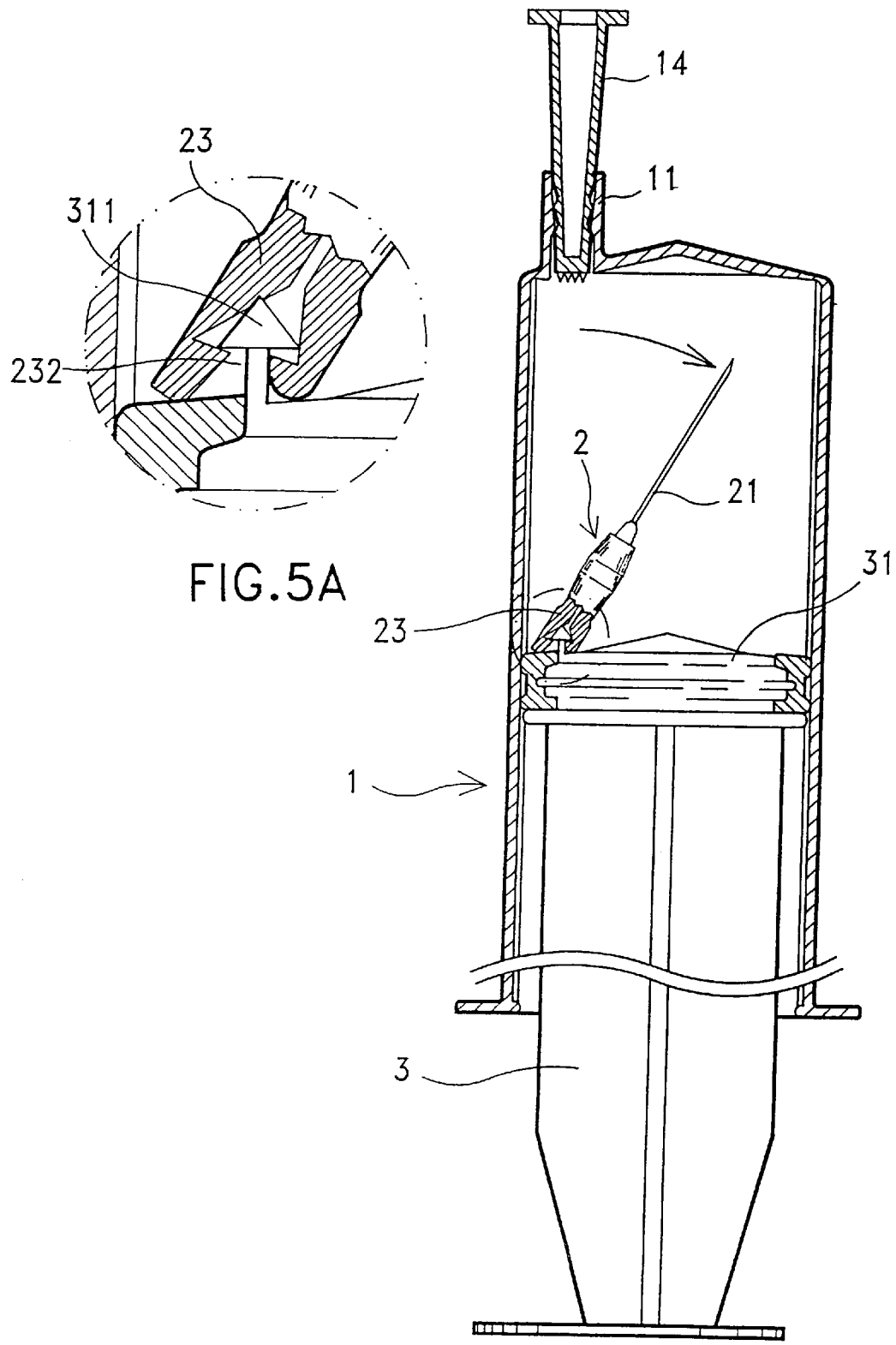
FIG. 5 illustrates the present invention with a needle retracted into the syringe barrel.
FIG. 5A is an enlarged sectional view of the bottom of the needle holder of FIG. 5.

As shown in FIGS. 5 and 5A, when the plunger 3 is pulled backward, the needle unit 2 is pulled into the barrel 1. The inclined bottom surface of the connecting stem 23, the inclined arrowhead shaped mortise 231, and the conical surface of the plunger head 31 make the needle 21 incline to misalign the needle unit 2 with respect to the reduced tubular outlet 11. According to the results of many experiments, the needle 21 inclines mainly because of the inclined bottom surface of the connecting stem.

Figure 6:
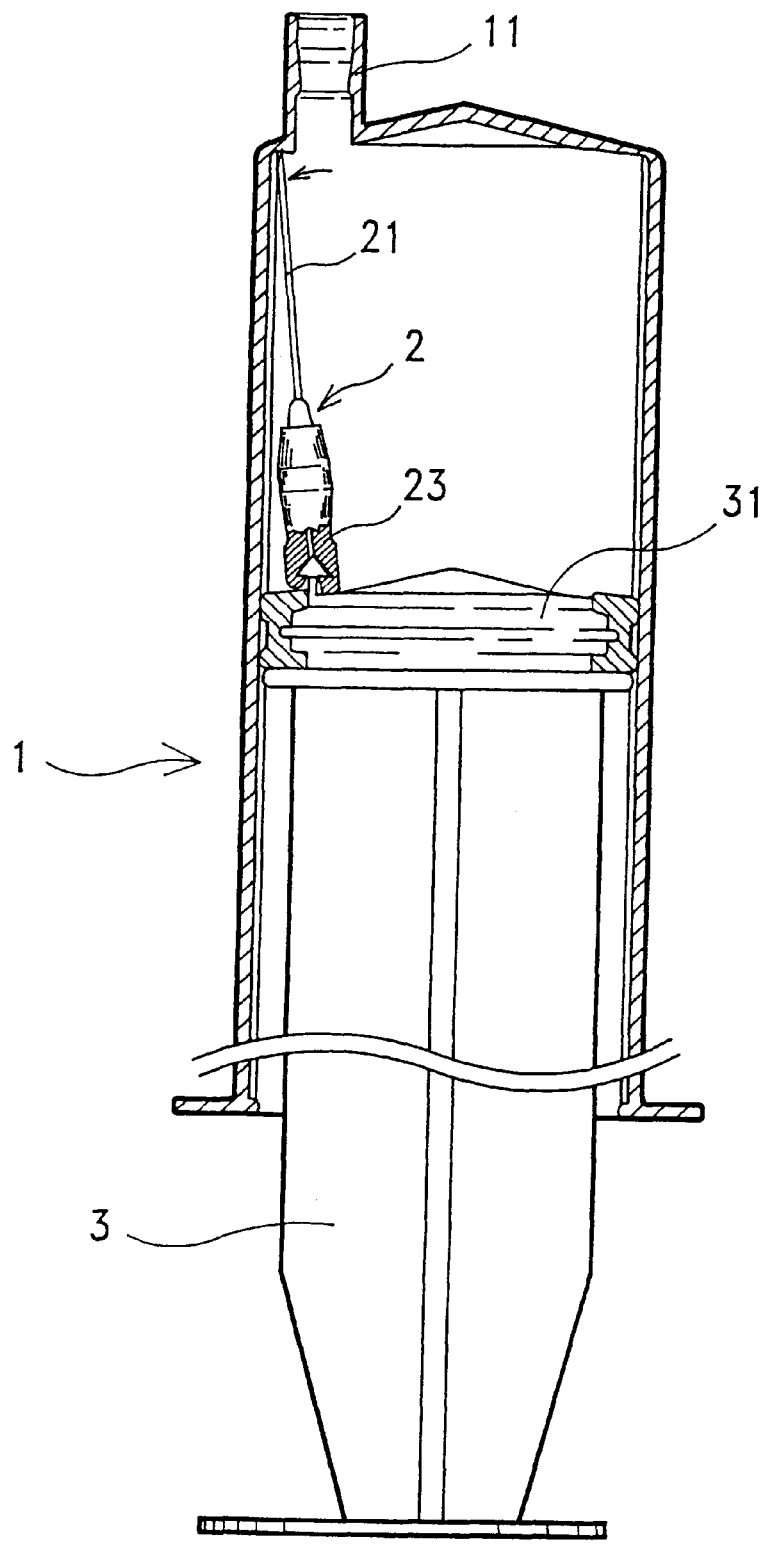
FIG. 6 shows a blocking effect of an outwardly protruding needle in the present invention; and, FIG. 6A is an illustration showing the damage to a needle inside the barrel when the plunger of the present invention is pushed forward.
Figure 6A:
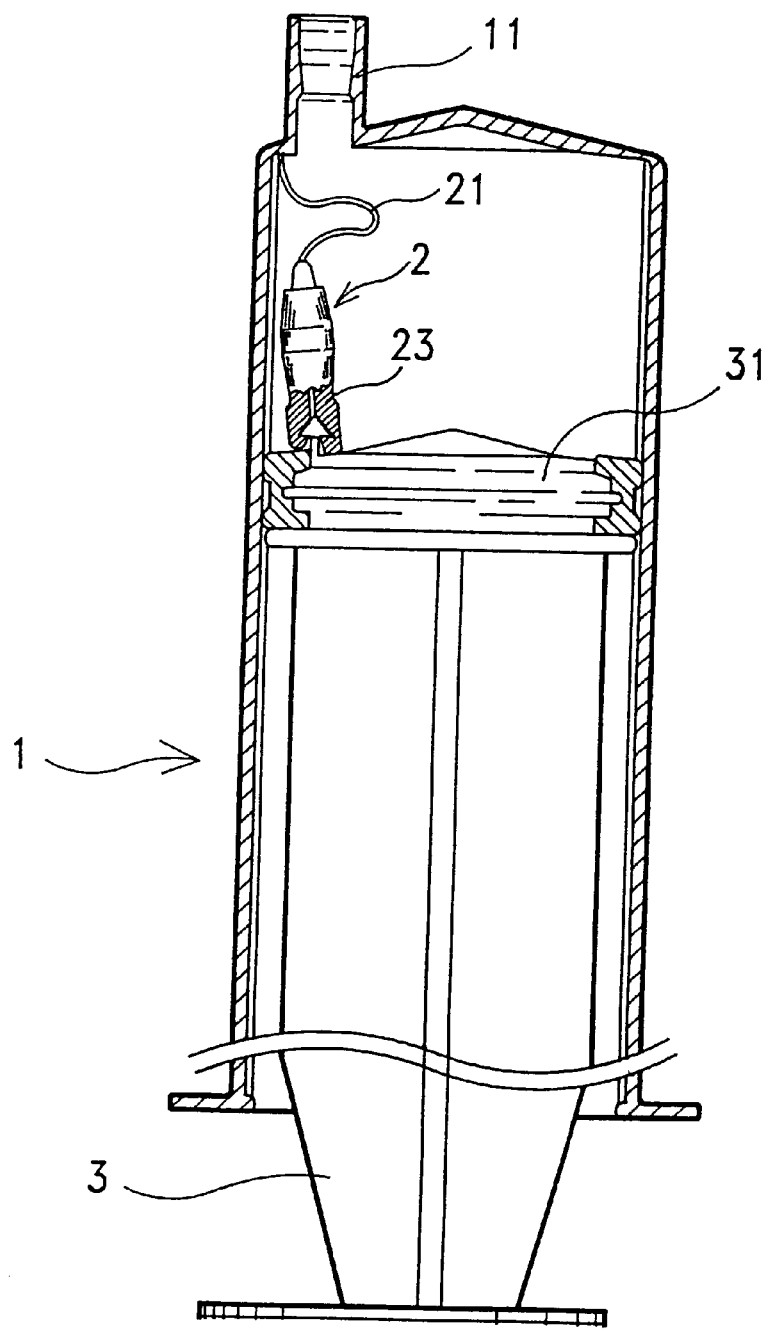

Referring additionally to FIGS. 6 and 6A, when the plunger 3 is subsequently pushed forward again the needle 21 cannot be forced out of the barrel 1. A needle cap 14 is inverted and inserted into the outlet 11 of the barrel 1, as shown in FIG. 5.

The above embodiments can be modified by any person skilled in the art without departing the spirit and scope of the accompanying claims.

What is claimed is:

1. A safety syringe for intravenous injection, comprising:
    a barrel having a conically shaped front portion and an opposing rear portion with an outwardly extended flange formed thereat, said barrel having a bore formed therein and said rear stem having an opening formed in open communication with said bore, said barrel having a pair of guide strips formed on a wall surface interior to said bore and a reduced tubular outlet eccentrically disposed on said conically shaped front portion and in open communication with said bore;

a needle unit having a spindle shaped needle holder releasably coupled to said tubular outlet and a cannulated needle affixed to said needle holder to extend from a first end thereof, said needle holder having a second end and a connecting stem extending therefrom, said connecting portion having an inclined bottom surface and an opening extending from said bottom surface with an arrowhead shaped mortise formed in said opening and inclined with respect to an axis of said needle;

a plunger slidingly disposed in said bore of said barrel, said plunger having (a) a plunger head having an upper conical surface, (b) an arrowhead shaped tenon eccentrically disposed on said plunger head and extending from said upper conical surface thereof in aligned relationship with said mortise of said connecting stem, (c) a sealing ring circumscribing said plunger head, and (d) a supporting plate disposed beneath said plunger head and supporting said sealing ring, said supporting plate having a pair of guide notches formed therein for respectively receiving said pair of guide strips therein, said plunger being displaced toward said front portion of said barrel to express a fluid from said barrel and engage said mortise with said tenon, subsequent displacement of said plunger toward said rear portion of said barrel thereby displaces said needle unit into said bore of said barrel and said needle set being offset with respect to said tubular outlet by cooperation between (i) said inclined bottom surface of said connecting portion, (ii) said conical surface of said plunger head, and (iii) said inclined mortise; and, a tubular needle cap having a closed distal end for insert into said tubular outlet subsequent to said needle unit being displaced into said bore.

* * * * *